United States Patent [19]
Zarge et al.

[11] Patent Number: 5,289,373
[45] Date of Patent: Feb. 22, 1994

[54] METHOD AND APPARATUS FOR REAL-TIME TRACKING OF CATHETER GUIDE WIRES IN FLUOROSCOPIC IMAGES DURING INTERVENTIONAL RADIOLOGICAL PROCEDURES

[75] Inventors: Jonathan A. Zarge, Woburn, Mass.; Nelson R. Corby, Jr., Scotia, N.Y.

[73] Assignee: General Electric Company, Schenectady, N.Y.

[21] Appl. No.: 800,377

[22] Filed: Nov. 29, 1991

[51] Int. Cl.$^5$ .............................................. G06F 15/00
[52] U.S. Cl. ................................. 364/413.13; 382/6; 382/56
[58] Field of Search ................. 364/413.13; 382/6, 16, 382/55, 56, 34, 37; 358/88, 98; 250/458.1; 128/656

[56] References Cited

U.S. PATENT DOCUMENTS

| | | | |
|---|---|---|---|
| 4,459,990 | 7/1984 | Barnea | 128/656 |
| 4,922,332 | 5/1990 | Taniguchi et al. | 382/55 |
| 4,998,972 | 3/1991 | Chin et al. | 358/98 |
| 5,036,464 | 7/1991 | Gillies et al. | 358/98 |
| 5,119,445 | 6/1992 | Suzuki et al. | 382/55 |

OTHER PUBLICATIONS

Thesis-Three Dimensional Navigation Assist for Interventional Radiological Procedures, submitted to the Graduate Faculty of Rensselaer Polytechnic Institute on Dec. 1990, Jonathan A. Zarge.

*Primary Examiner*—Roy N. Envall, Jr.
*Assistant Examiner*—Frantzy Poinvil
*Attorney, Agent, or Firm*—Paul R. Webb, II

[57] ABSTRACT

An apparatus for real-time tracking of a catheter guide wire in a patient undergoing an interventional radiological procedure includes an image processing unit for processing digitized fluoroscopic images from a fluoroscope image output. The image processor utilizes a novel algorithm for locating the image of a catheter in the fluoroscopic image. The image processor creates a two-dimensional model of the catheter for dynamic display on an operating room live image video monitor.

8 Claims, 11 Drawing Sheets fig. 1 fig. 2 fig. 3 fig. 4 fig. 5 fig. 6 fig. 8 fig. 10

```
CHAIN 1: 1  2  3  4  5  6  7  8  9  10  11  12  13  22
CHAIN 2: 22  14  15  16  17  18
CHAIN 3: 22  19  20  21
CHAIN 4: 22  23  24  25
CHAIN 5: 25  26  27  28
CHAIN 6: 25  29  39  31  32  33  34
CHAIN 7: 35  36  37  38
CHAIN 8: 39  40  41  42  43  44  45  46  47  48  49  50  51  52  53  54
``` fig. 7 fig. 9a fig. 9b fig. 9c fig. 11a fig. 11b fig. 12
```
V           9 10 16
V           9 10 11 12
V           9 10 11 13 14
V           9 10 11 13 15 17
V           9 10 11 13 18
V     2 4 5 8 10 16
V     2 4 5 8 10 11 12
V     2 4 5 8 10 11 13 14
V     2 4 5 8 10 11 13 15 17
V     2 4 5 8 10 11 13 18
V     1 4 5 8 10 16

• • •  (18 PATHS OMITTED)  • • •

V     7 5 8 10 16

V           3 1 2 6 5
I           3 1 2 6 4 3
I           3 1 2 6 4 1
V           3 1 2 7 8 9 10 12
V           3 1 2 7 8 9 10 11
V           3 1 2 7 8 11 12
V           3 1 2 7 8 10 9
V           3 1 2 7 9 8 10 12
V           3 1 2 7 9 8 10 11
V           3 1 2 7 9 11 12
V           3 1 2 7 9 1 10 9
V           3 1 2 7 10 12
V           3 1 2 7 10 11 8
V           3 1 2 7 10 11 9
I       5 4 1 2 6 5
I       5 4 1 2 6 4 3
I       5 4 1 2 6 4 1
V       5 4 1 2 6 8 9 10 12

• • •  (163 PATHS OMITTED)  • • •

I 9 11 10 7 6 4 1 2 7 10 11 9
``` fig. 13 fig. 14

METHOD AND APPARATUS FOR REAL-TIME TRACKING OF CATHETER GUIDE WIRES IN FLUOROSCOPIC IMAGES DURING INTERVENTIONAL RADIOLOGICAL PROCEDURES

This invention relates generally to Interventional Radiological procedures and more specifically to a method and apparatus for providing the physician performing the procedure with an improved fluoroscope display by tracking the movement of a catheter within a patient and displaying the catheter in an enhanced form on the fluoroscope display.

RELATED APPLICATIONS

The present application is related to commonly assigned and copending U.S. patent application Ser. Nos. 07/800379 (RD-20,472) and 07/800374 (RD-20,473) entitled respectively, A Method for Reducing X-Ray Dosage During Fluoroscopic Examinations and Method and Apparatus for Real-Time Navigation Assist in Interventional Radiological Procedures both filed Nov. 29, 1991.

BACKGROUND OF THE INVENTION

Interventional Radiology (IR) is a rapidly growing branch of medicine which uses medical imaging systems such as Computer Tomography, Magnetic Resonance, X-ray and fluoroscopy for therapeutic as well as diagnostic purposes. In IR, a physician wishes to guide a catheter to a remote site within the body for the purpose of making measurements, retrieving samples (biopsy), effecting therapeutic actions (for example, angioplasty of an artery wall), or blocking of an artery feeding a tumor (embolization). The catheter is a thin tube (2-6 mm diameter) on the order of 1 meter long which contains a number of interior passages (depending on design) and which is guided by a flexible, removeable, X-ray opaque internal guide wire.

The circulatory system can be thought of as a tree-like structure fanning out from a central arterial tube at the heart. The diameter of the main aorta is on the order of 2-4 cm. Beginning with the bifurcation of the main aorta, each subsequent branch forks or bifurcates into two or more smaller diameter branches. Eventually at the cellular level the arterial diameter narrows to that of an individual red blood cell. The veinous system is responsible for collecting the blood cells from the capillaries for eventual return to the heart. The geometry of the veinous network is the inverse of the arterial system, with small tubes merging to form larger tubes which merge to form still larger tubes. While there is considerable similarity in topology and geometry among individuals at a gross level, at a detailed level the vascular system has a complex topology with a tortuous three-dimensional geometry which is unique to each individual.

The goal of an IR procedure is to deliver the working end of a catheter to an internal site within the body of the patient. The vascular system is used to physically contain the catheter and to act as the conduit along which the catheter progresses. Access to the vascular system is via a puncture with a tubular sleeve which remains in place during the procedure. The catheter and guide wire are threaded through the sleeve.

The fluoroscope (a 30 Hz X-ray machine) is the primary tool used by the physician to help guide the catheter. In many cases, his knowledge of general vascular anatomy, his experience, and the "in-process" fluoroscope images provide sufficient information to enable the physician to reach the target site. Typically, the images are formed at a rate of 30 per second and displayed on a TV-like monitor.

The most prominent feature in a fluoroscopic image is the radio-opaque catheter guide wire. When the guide wire is inserted into the catheter, the thin guide wire shadow in the fluoroscopic image indicates to the physician the location of the catheter. When the guide wire tip is extended beyond the end of the catheter (before the actual catheter is advanced), the guide wire shadow indicates one possible future path of the catheter. Often, due to the amount of tissue through which the X-rays must penetrate or the small size of the guide wire, the guide wire "shadow" is not easily distinguishable from the surrounding tissue.

What is needed is a catheter guide wire enhancement system that would aid the physician in ascertaining the position of the catheter guide wire in fluoroscopic images. The system would create a two-dimensional model of the guide wire in the image plane, and overlay the highlighted two-dimensional model on top of the live fluoroscopic images at a rate of 30 frames per second.

A major benefit of this invention is that a lower dose of X-rays can be used since the radiologist can work with a "poorer" image.

SUMMARY OF INVENTION

In accordance with the present invention, there is provided a computer based system that allows a physician to more rapidly guide a catheter through the circulatory system of a patient undergoing a diagnostic or therapeutic interventional radiological procedure. The system automatically locates the catheter guide wire in a digitized fluoroscopic image, creates a two-dimensional model of that guide wire and displays the model in an informative and useful way that assists the physician during the procedure. One method of display is overlaying a brightly colored guide wire model on top of the live fluoroscopic images.

Such a system would reduce the time required for IR procedures which would allow more commonplace procedures to be completed in less time or would allow more complex procedures to be attempted. The speed-up would result in less X-ray dosage to the physician and to the patient.

DESCRIPTION OF THE INVENTION

Figure 1:
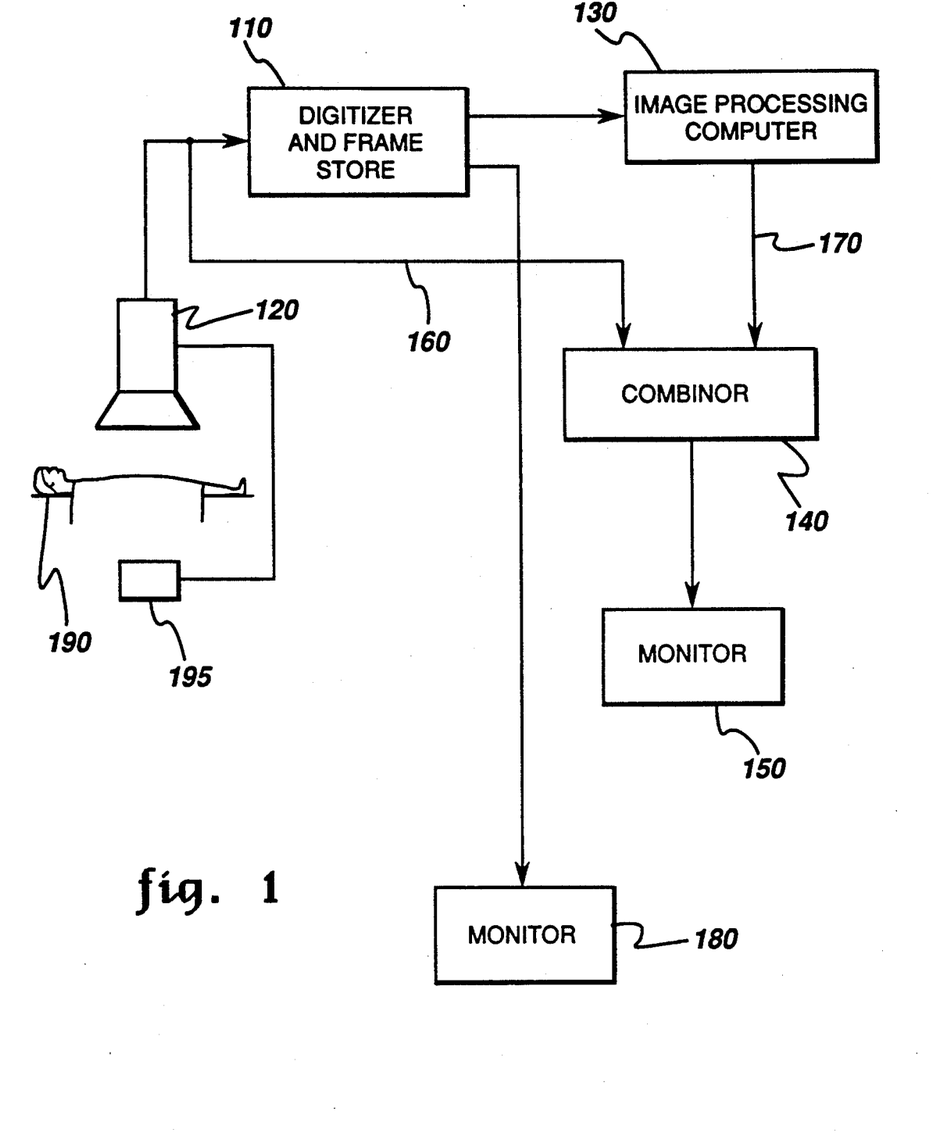
FIG. 1 is an apparatus diagram of a catheter tracking system in accordance with the present invention.

FIG. 1 is an apparatus diagram of a catheter tracking system in accordance with the present invention. A digitizer 110 is operably connected to the video output of a fluoroscope 120. Digitized fluoroscopic images are processed in the image processing computer 130 as will be described in more detail below. The combinor 140 is a video circuit which provides the live image output monitor 150 with either the standard video output signal 160 from the fluoroscope or a signal that combines the signal 160 with the enhanced digital output 170 corresponding to the location of the catheter as determined in the image processing computer 130. The resulting video display at 150 is a standard fluoroscope image with an enhanced image of a catheter superimposed thereon. A standard stored image display 180 is also shown and is used also in prior art systems for displaying a fluoroscope image that has been stored and selected for viewing by the physician.

A patient 190 is shown positioned between an X-ray source 195 and an image detection screen 120. These two elements are part of all prior art fluoroscope systems. In prior art fluoroscopes, the signal generated by the detection screen is fed directly to an output monitor such as 150 and provides the physician with a TV like picture of what is being imaged. Many prior art systems also have the ability to digitize and store image frames which can be displayed as a still picture on another monitor such as 180 in FIG. 1. The present invention provides an improved method and apparatus in which an image processing computer 130 operates on digitized image frames in digitizer 110 to create a 2D model of a catheter in patient 190 being imaged. Digitized images typically consist of pixels (discrete picture elements) which vary in brightness on some scale from black to white. A combinor 140 allows the 2D model image to be superimposed on the standard fluoroscope video output displayed on monitor 150.

Figure 2:
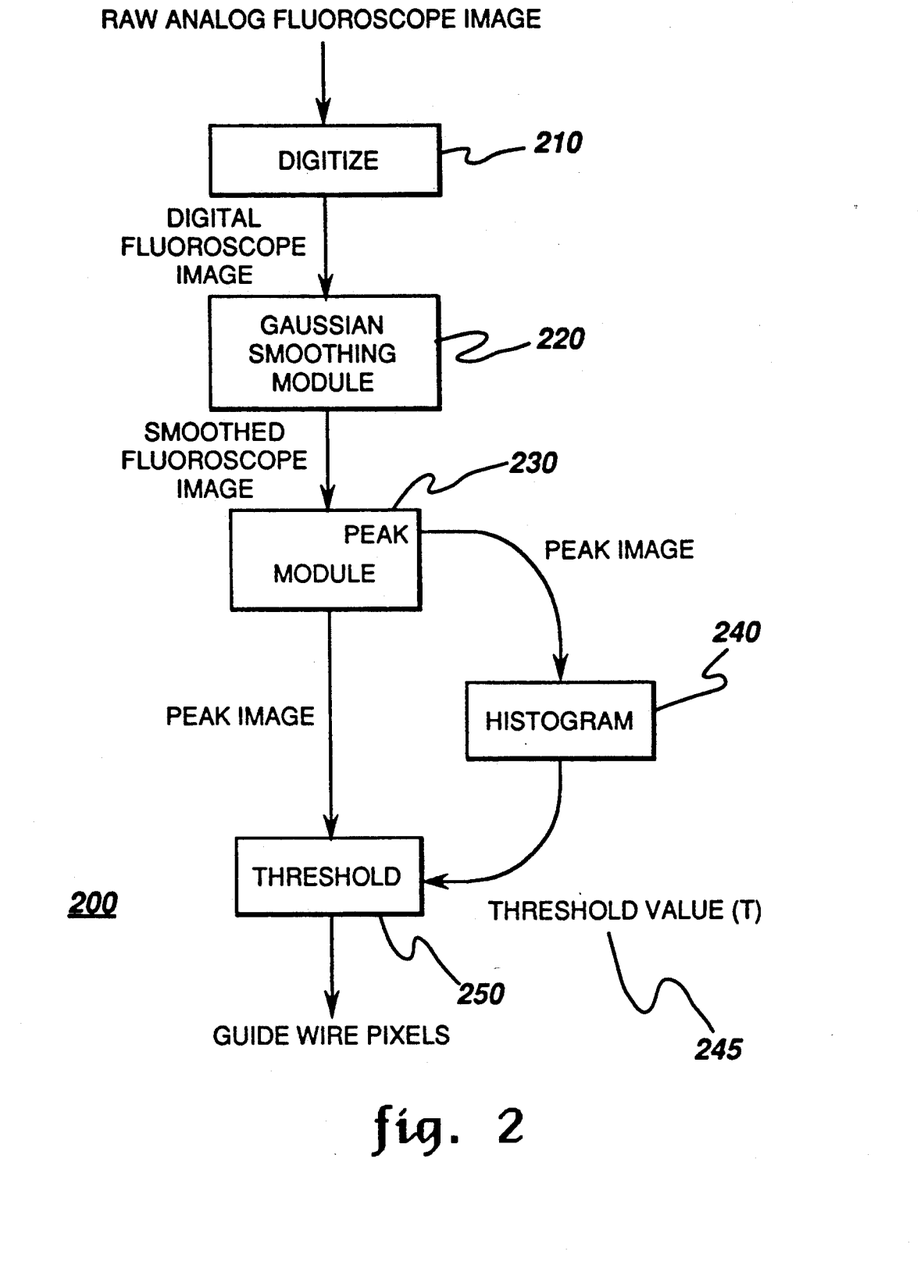
FIG. 2 is a flowchart for peak image finding.
Figure 3:
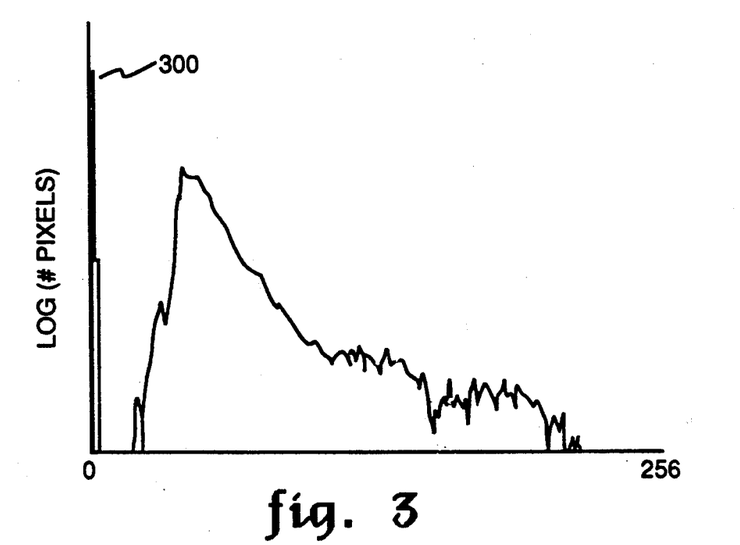
FIG. 3 is the output of the peak filter algorithm on the sample image.

The image processing which computer 130 performs is broken up into two parts, peak finding (shown in FIG. 2) and two-dimensional model building (shown in FIG. 3). The goal of the peak finding module is to determine which pixels (two-dimensional picture elements) in the images correspond to the catheter guide wire. Next, these pixels are scanned for connectivity to other guide wire pixels which eventually results in a two-dimensional model (linked list of pixels) of the catheter guide wire in the image plane.

FIG. 2 shows the peak finding algorithm used to locate the catheter guide wire pixels. First the image is digitized at block 210. Next, the image is smoothed with a 5×5 Guassian kernal at block 220. Second derivative values for each pixel are computed in the four principle directions; horizontal, vertical, and the two diagonals. Rotated variations of [1-2 1] are used. The [1-2 1] kernals implement the second derivative operation. The peak module 230 converts a raw image into a peak image. For every pixel P in the image, the maximum of the four second derivatives is computed by convolving the image with the kernals described above and taking the maximum of those four values. Next, each pixel is tested to determine if it is a maximal gradient point in the direction from which the maximal value was discovered. If it is, the value of pixel P is set to that maximal value, if not, P is set to a low value (lower than any of the maximal gradient values). The resulting image is a peak image of the original raw fluoroscopic image.

Figure 4:
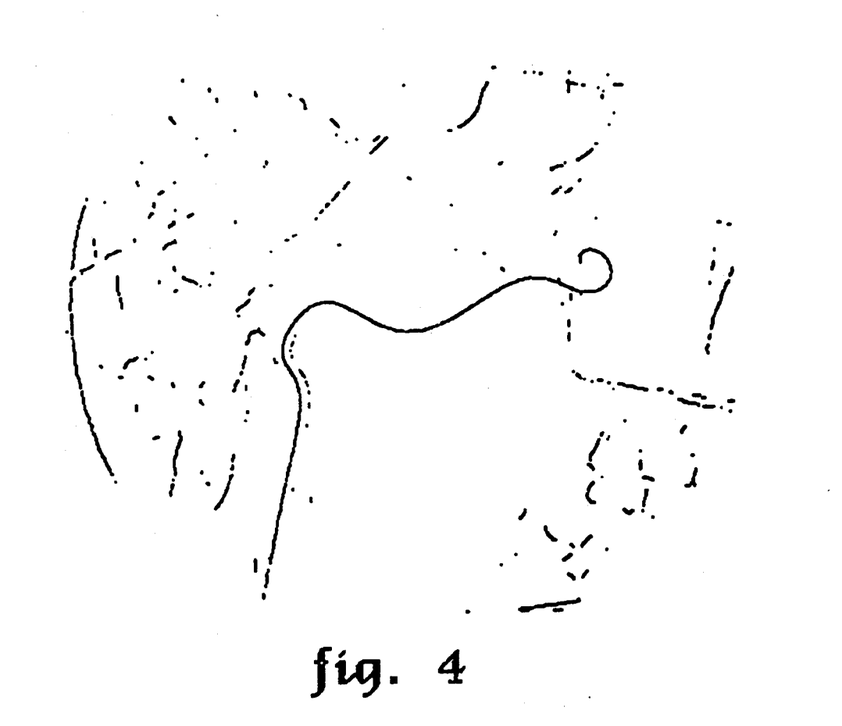
FIG. 4 is a peak image histogram for the sample image.

The next step 250 is to find the proper threshold value for the peak image. For this, a histogram 640 is necessary. FIG. 3 shows a sample histogram. The histogram reveals that there is a large spike 300 of pixels whose value is at the low end of the range. Besides this spike at the minimum value, a more "normal" distribution of values exists over the remaining values in the peak image. Before the threshold value is computed, the image is masked to blank out all pixels near the edge of the image and outside of the circular region that defines the boundary of the fluoroscope data. Then, the proper threshold, T (245 in FIG. 2), is computed based on the histogram of the peak image data. In a preferred implementation, T is set to the mean plus two standard deviations (the mean and standard deviation for the peak image are computed based on peak image pixel values except those pixels whose value is at the minimum spike). FIG. 4 shows the resulting binary image. There are small breaks in the guide wire pixel chains but this problem will be discussed and solved hereinbelow. This binary peak image is the input for the two-dimensional model creation module shown in FIG. 3.

Figure 5:
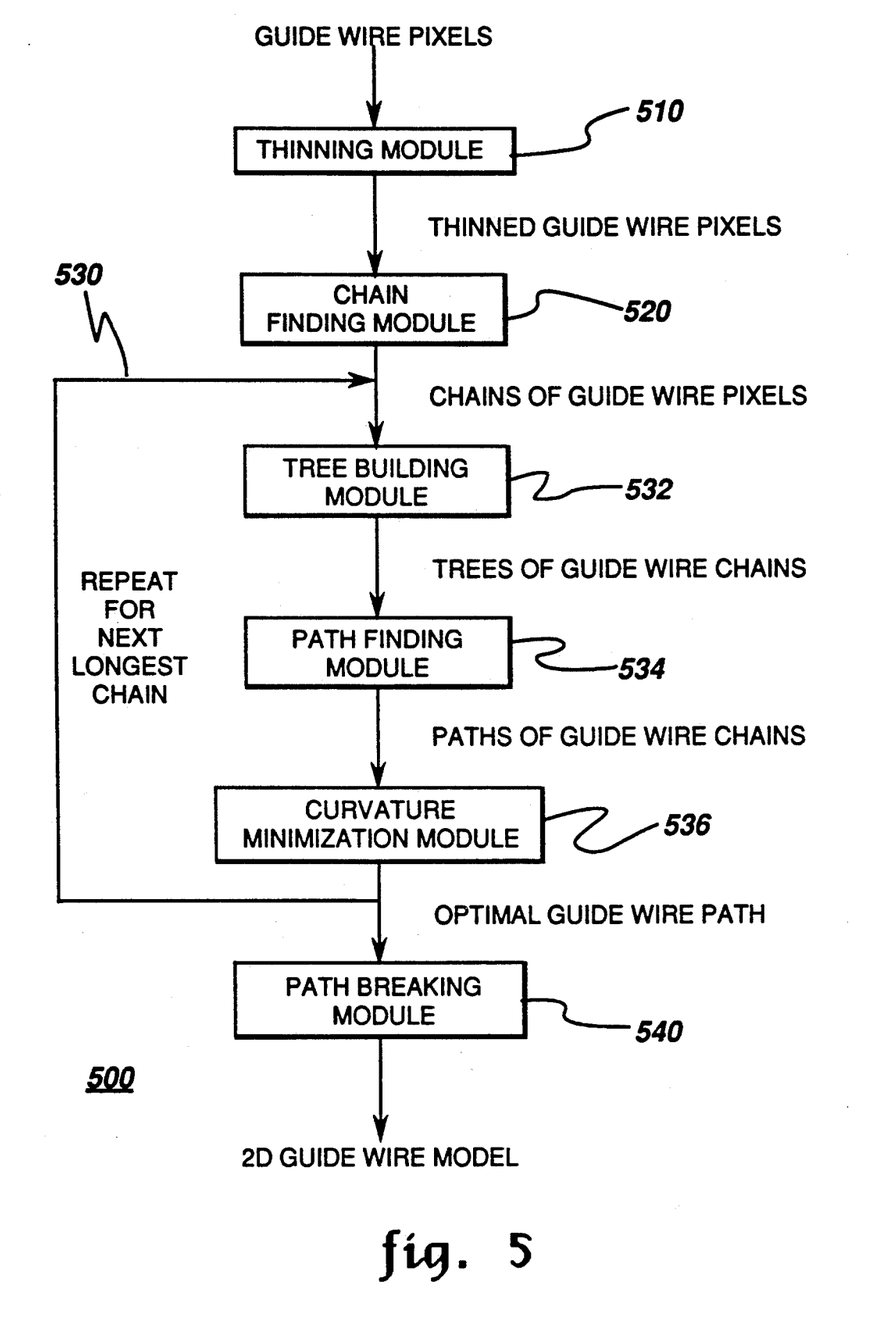
FIG. 5 is a flowchart for two-dimensional model creation.

FIG. 5 shows a two-dimensional model creation module 500. The goal of the two-dimensional model creation module 500 is to construct a two dimensional model of the catheter guide wire in the image plane. This is accomplished by several smaller modules shown in FIG. 3. The image is first thinned at block 510 so that all the lines in the image are only one pixel wide. Then, chains of pixels are identified at 520. Next, a set of longest connected paths is compiled from which the path with the least amount of curvature is selected (loop 530). Finally, this optimal path is broken into segments at 540 (based on local curvature) yielding a set of ordered vertices which can be saved as the two-dimensional catheter guide wire model in the image plane. Each of these modules will now be described.

The first step 510 in two-dimensional model creation is thinning the peak image pixels in such a way that the genus of the image remains unchanged. The genus of an image is defined as the number of separated regions in an image. The neighbors of each pixel are scanned to determine if removing the pixel (setting it to the background color) will change the genus of the image. If removing the pixel will change the genus or if the pixel is an endpoint of a chain of pixels, then the pixel remains unchanged; otherwise, it is removed. This thinning process repeats until no pixels may be removed from the image.

Figure 6:
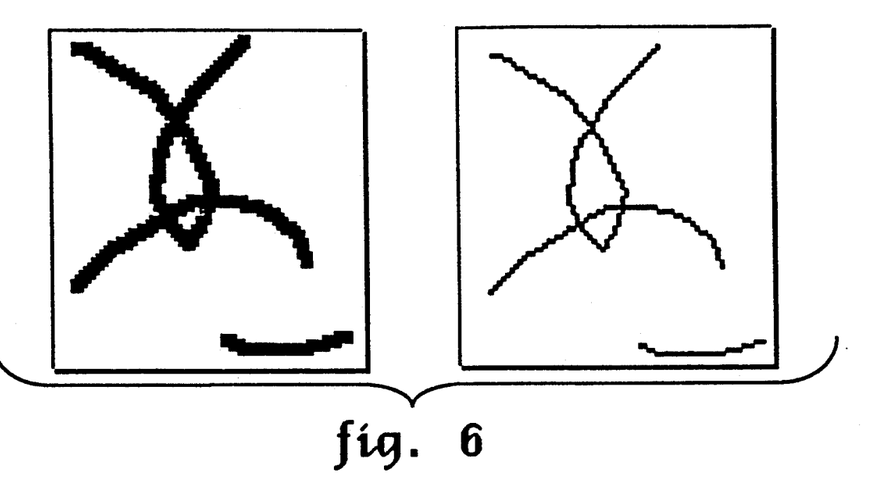
FIG. 6 illustrates thinning of a test image.

FIG. 6 shows two enlargements of a test image; one before thinning (on the left) and one after thinning (on the right). The square blocks in the thinned image on the right represent one pixel. Thinning the peak image is necessary for the chain finding module to function properly.

Referring again to FIG. 5, the pixels in the thinned peak image must be ordered into chains of pixels at block 520. This algorithm first examines the eight neighbors of each "on" pixel (not the background color) and counts the number of "on" neighbors of that pixel. If a pixel has two neighbors it is designated as a normal pixel; otherwise the pixel is designated as a juncture pixel. Therefore, ends of chains and intersection points become juncture pixels.

Figure 7:
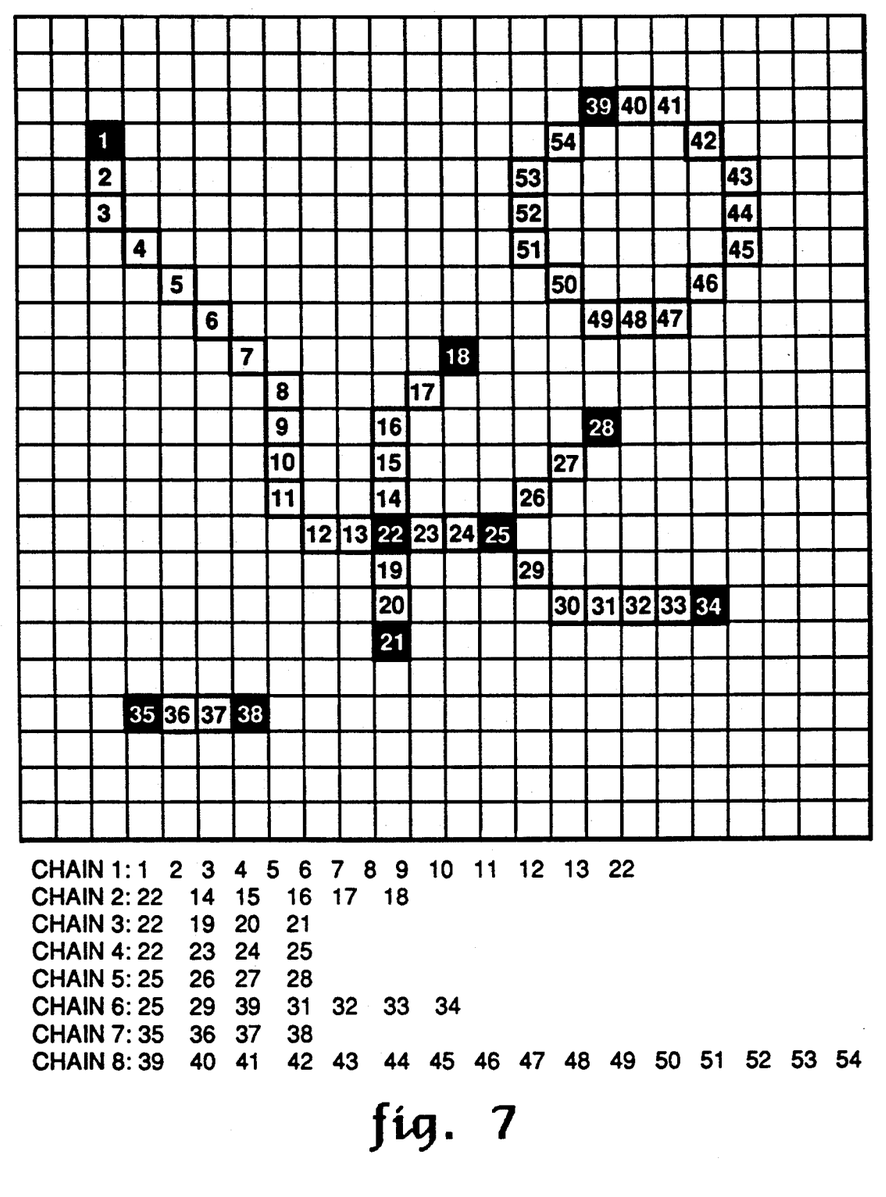
FIG. 7 illustrates chains of pixels in a test image.

FIG. 7 shows a small portion of a binary peak image; each box represents a pixel and the number inside of each box indicates its identification number. Normal pixels have black numbers in white boxes, juncture pixels have white numbers in black boxes, and background pixels have no numbers. In the chain finding module 720, chains are formed by traveling from one pixel to another starting at a juncture and ending at a juncture. The starting juncture pixel is designated the head of the chain and the ending juncture pixel is designated the tail of the chain. After all juncture pixel neighbors are processed, any remaining pixels are designated as being members of cycles; these chains of pixels do not contain any junctures. These pixels are processed in a special way. Within each cycle a random pixel is chosen to become a juncture pixel. At this point these cycles can be treated as the non-cyclic chains and traversed in the same way, from juncture to juncture (the starting and ending junctures are the same juncture; thus, the head and the tail of the chain are identical). The circle of pixels in the upper right hand corner of FIG. 7 exemplify a cycle. Using this algorithm, eight chains would be found in the image in FIG. 7; the chains are listed under the grid.

Referring again to FIG. 5, steps 532-536 find a group of chains which form the optimal path corresponding to the catheter guide wire. Here, optimal is defined as the longest semi-connected group of chains with the minimum curvature (semi-connected will be defined below). This is accomplished in three parts: tree building 532, path finding 534, and curvature minimization 536. In the tree building module 532, the proximity relationships between chains is computed by organizing the chains into a tree-like structure. This is necessary because the peak finding module usually does not yield a continuous chain of pixels which corresponds to the catheter guide wire. Therefore, chains whose endpoints are semi-connected to each other become candidates for being members of the two-dimensional model of the guide wire.

A tree is comprised of a number of nodes. A node can have one parent and a number of children. There are three types of nodes: roots, which have children but not a parent, regular nodes, which have children and a parent, and leaves, which do not have children but do have a parent. In this implementation, each node corresponds to a chain in the image. The tree building process starts by first finding the longest chain from the chain finding module. This chain will serve as the root node for two trees: one tree connected to its head pixel and another tree connected to its tail pixel.

Figure 8:
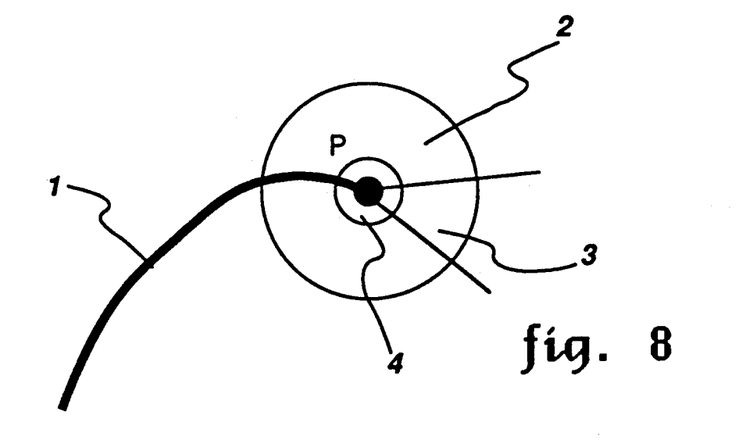
FIG. 8 is an illustration of semi-connected chains.

Building a tree is a simple recursive process which starts from a chain and works until there are no more chains that can be processed. Before the tree building process is described, the definition of "semi-connected" is supplied. FIG. 8 shows a typical scenario. The thick black line represents a chain of pixels (chain 1); the end of the chain marked by a filled black circle (pixel P) represents the pixel against which other chains are compared. Two larger circles surround this endpoint. The smaller circle forms the boundary of the principle search region. If any other chain endpoint lies in this region, it is semi-connected to chain 1. The larger circle represents the secondary search region. If the endpoint of any other chain lies in this region (but not in the principle search region) it is semi-connected to chain 1 only if it also lies in the region bounded by the two rays emanating from P. The rays are chosen such that the bisecting ray between the two rays is parallel to the direction of the end of chain 1. In this implementation the radius of the principle search region is five pixel units, the radius of the secondary search region is three times the radius of the principle search region, and the angle between the rays is one radian. Only if a chain's endpoint lies in either of these two regions is it a candidate for becoming a child of chain 1. Thus, while chains 3 and 4 might become children of chain 1, chain 2 cannot.

Figure 9A:
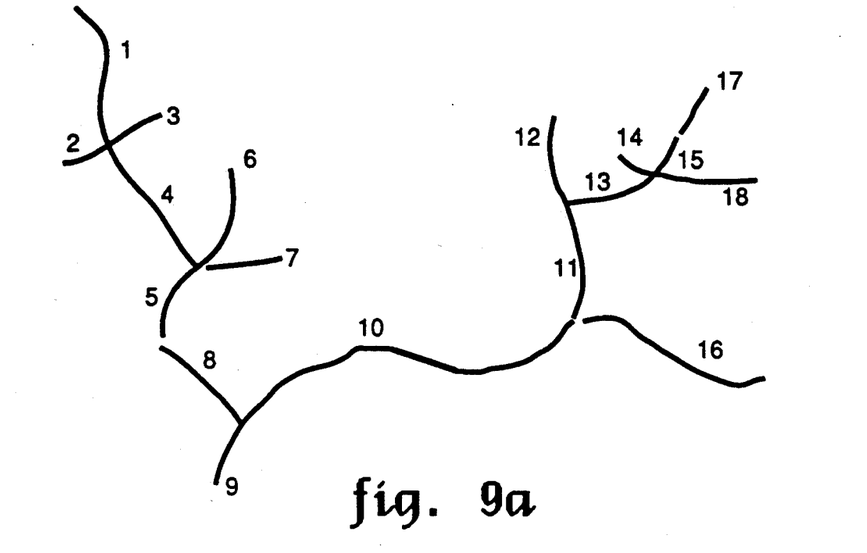
FIGS. 9a-9c illustrate tree building on a test image.
Figure 9B:
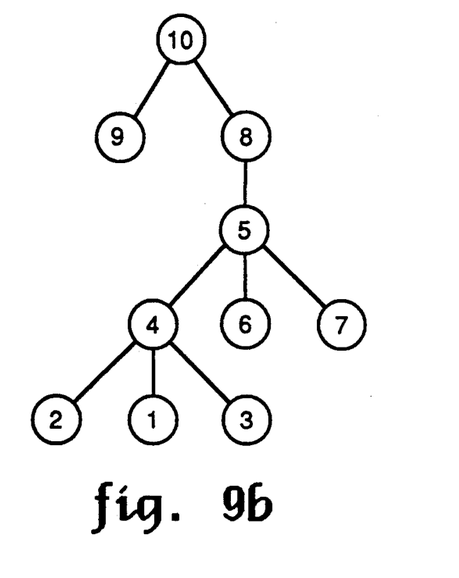
Figure 9C:
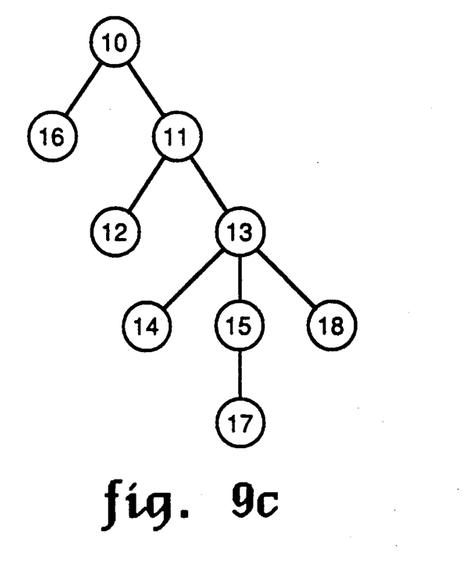

A few examples of tree building will explain the process. Examples of the tree building process on a test image is shown in FIG. 9. The chains are shown in FIG. 9a and the two resulting trees, one for the head pixel of the longest chain and one for the tail pixel, are shown in FIGS. 9b and 9c respectively. For simplicity, all chains which are relatively close to each other are considered to be semi-connected. In FIGS. 9b and 9c, child nodes are shown in the tree below their parent node and the numbers inside the nodes of the trees designate the chain to which the node corresponds. Chain 10 is the longest chain in the image so both root nodes correspond to chain 10.

Figure 10:
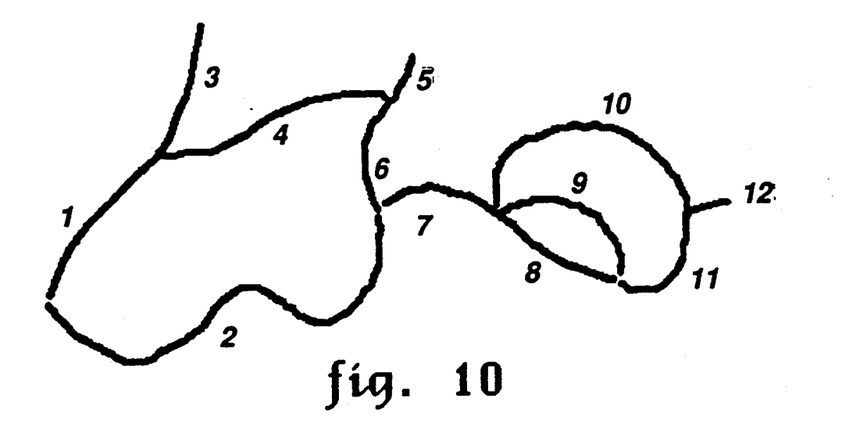
FIG. 10 illustrates a complex test image.
Figure 11A:
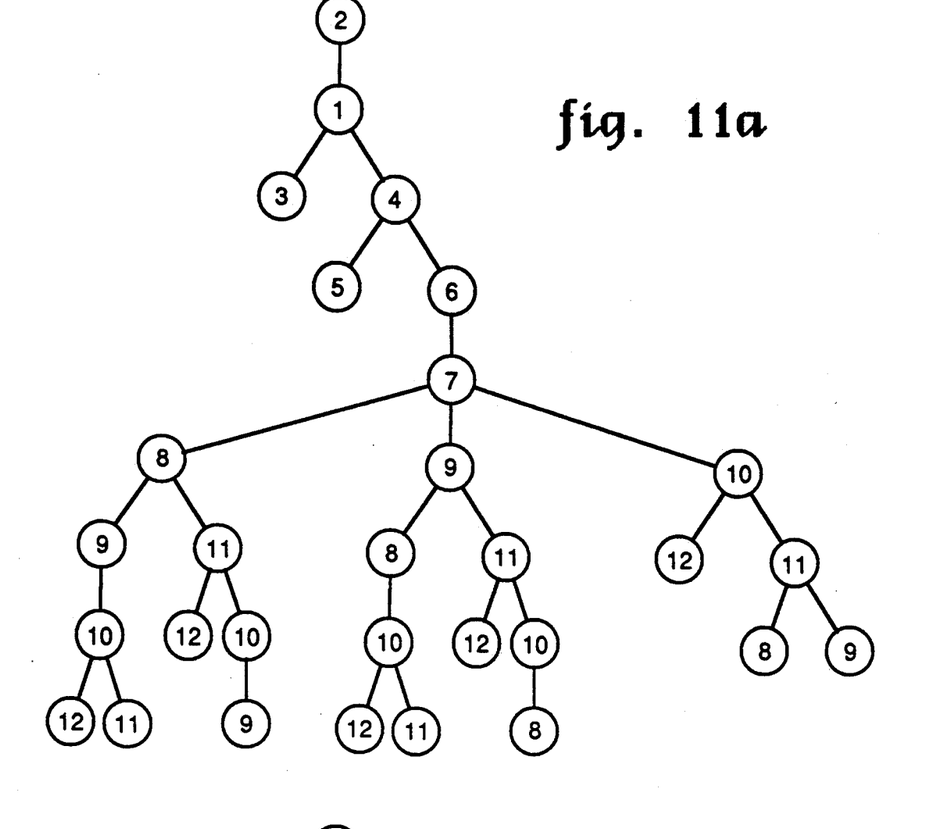
FIGS. 11a and 11b illustrate tree building on a complex test image.
Figure 11B:
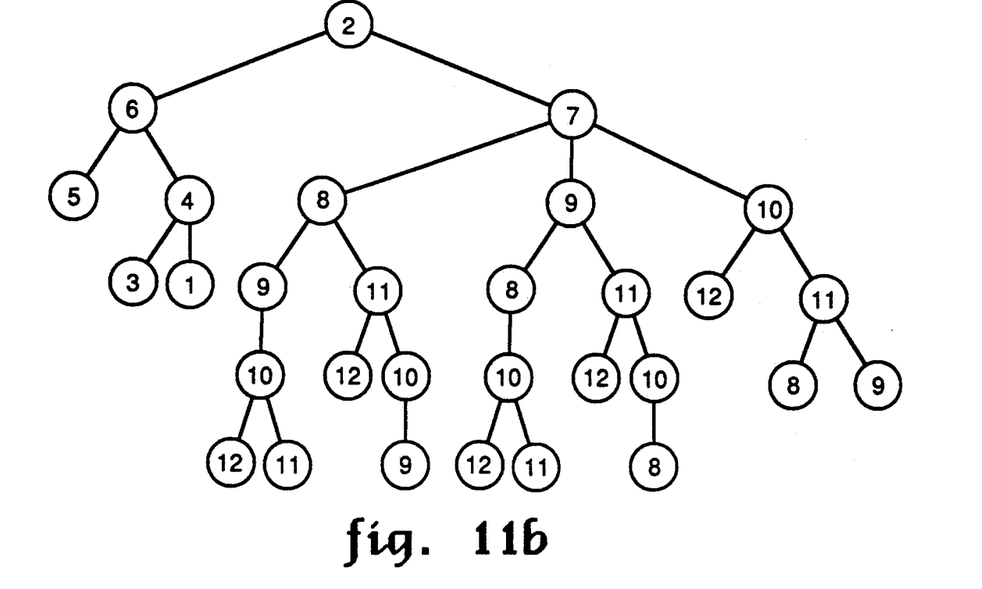

A more complex tree building example is next shown. FIG. 10 shows an image with fewer chains (12 compared with 17 in FIG. 9a) but much more complex trees (shown in FIG. 11a and 11b). The reason for this increased complexity is that the two trees formed from the endpoints of the longest chain (chain 2) are not disjoint sets; many chains appear in both trees. Also, some of the chains form loops which further complicate the process. FIG. 11b shows that there is one more constraint on the possible children of a chain in addition to being semi-connected. If chain B is semi-connected to chain A but chain B is an ancestor of chain A (parent, grandparent, etc.) then chain B cannot be a child of chain A. This prevents infinitely deep trees from forming. In FIG. 11b, once chain 9 has been designated as a child of chain 8, chains 8 or 7 cannot be children of 9 even though they are semi-connected to chain 9.

Figure 12:
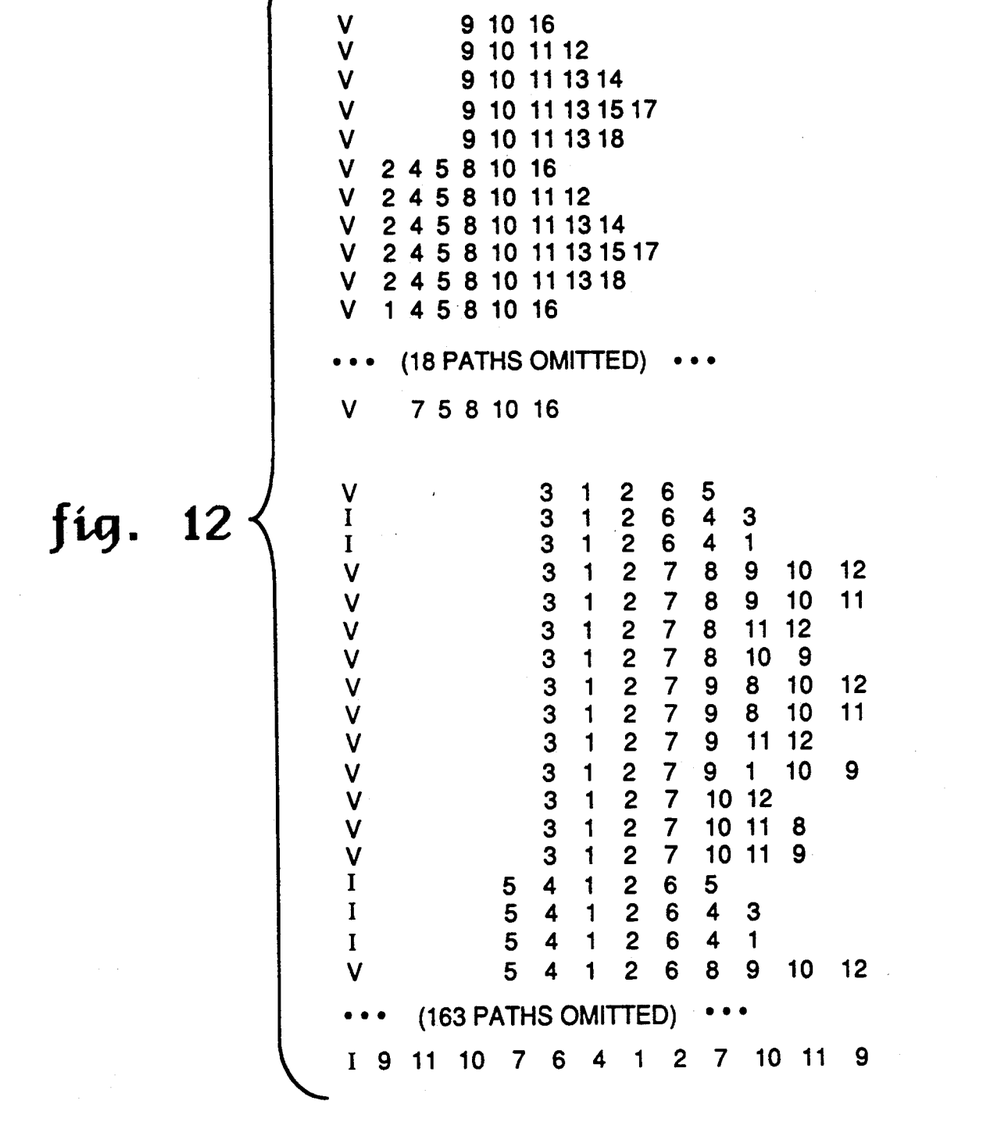
FIG. 12 illustrates paths derived from a simple test image and a complex test image.

After both trees have been constructed, the longest, valid path through the nodes of the trees is discovered. This is accomplished by performing a depth first search on both trees (head tree and tail tree) and testing the path between every leaf node in one tree to every leaf node in the other tree for length and validity. A path is invalid if a chain appears twice in the path (of course, the root chain can appear in both trees). In FIG. 9a, computing the paths is relatively simple. The upper portion of FIG. 12 shows some of the 30 paths generated by these trees in the order that they are generated; the letter at the beginning of the path indicates whether the path is valid (V) or invalid (I). The lower portion of FIG. 12 shows some of the 182 paths generated for the complex example in FIG. 10. The length of the valid paths are computed by summing together the lengths of their component chains. This longest path (or paths) is then checked by the curvature minimization module.

Figure 13:
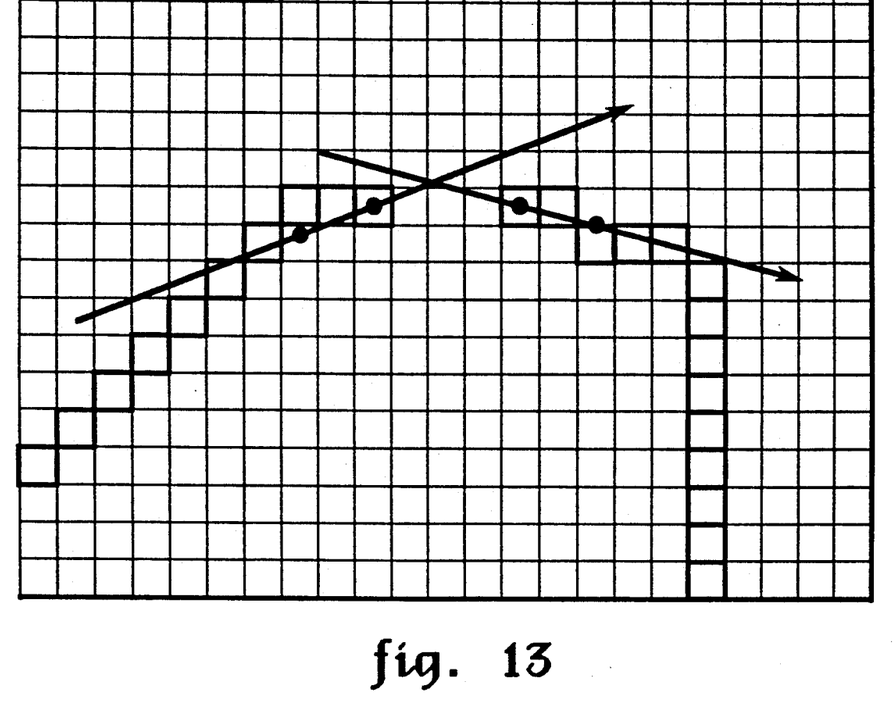
FIG. 13 illustrates angle calculation between two drains.

Referring again to FIG. 5, in the curvature minimization module 536, the curvature of all the longest paths is computed to determine which is the optimal path. The curvature of a path is the sum of the difference in angle between adjacent chains in the path. FIG. 13 shows how the angle between two chains is computed. The direction of an endpoint of a chain (shown as large arrows in the figure) is computed by calculating the average position of the N pixels closest to the endpoint of the chain (N=5). Then, the x and y values of the endpoint are subtracted from this average value to obtain a direction vector. The angle between the direction vector of one chain and the direction vector of the next chain defines the angle between two chains. Of the longest paths, the path with the lowest total curvature is designated the optimal path. This path is used by the path breaking module to compute the two-dimensional model of the guide wire.

As shown by loop 530 in FIG. 5, the method now scans all the chains to find the next longest chain and starts the tree building process again. The best path is stored in a global location so that when the new optimal path (derived from using the next longest chain as the root node for the head tree and tail tree) is computed it can be compared against the old optimal path. If the new optimal path is longer than the old optimal path then the new optimal path becomes the global optimal path. This process iterates until all chains are used as roots, or a predefined limit is reached.

Figure 14:
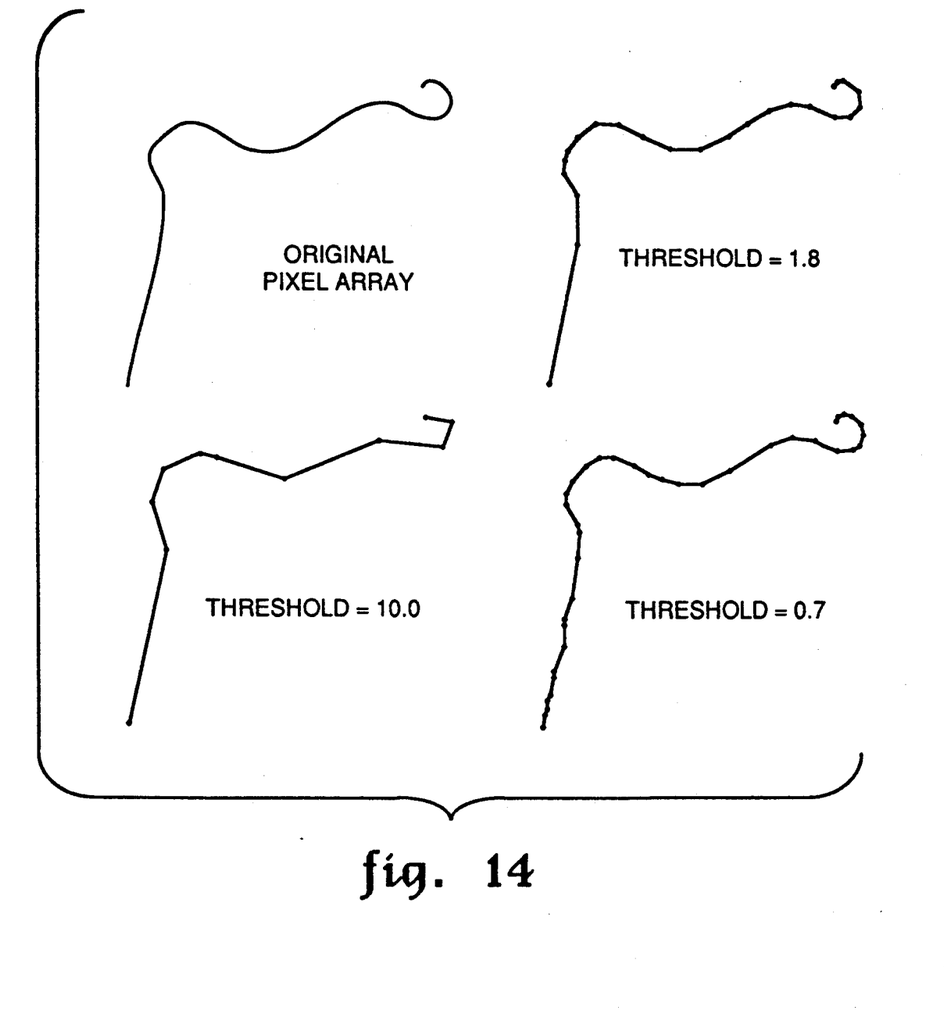
FIG. 14 illustrates the effect of varying thresholds on two-dimensional model complexity.

Finally, after the optimal path of chains has been found, the path is converted into a two-dimensional model at block 540. The two-dimensional model of the chains of pixels in the optimal path is a compact representation of the whole path; the model conveys the essence of the path without enumerating every pixel in the path. The representation of the two-dimensional model used in the present invention, is a simple, ordered, set of pixels which, when connected by lines, approximates the original path. Before any further processing, the pixels in the chains of the optimal path are dumped (in order) into an linear array of pixels. The array of pixels are recursively split into smaller and smaller segments until a certain threshold is reached; this threshold specifies the maximum distance (in pixel units) between the array of pixels and the two-dimensional model. If the distance between the line segment of the two-dimensional model and the array of pixels exceeds the threshold, the segment is split into two segments and the process is then invoked on the smaller segments. FIG. 14 shows the effect of different thresholds on the two-dimensional model created from the array of pixels. Higher thresholds will give coarse two-dimensional models but extremely small thresholds will yield two-dimensional models which too closely match the pixel grid. The dots in FIG. 14 correspond to vertices of the two-dimensional model and the lines connecting the blocks represent the ordered edges of the two-dimensional model. A threshold of three pixel units yields reasonable models.

While the present invention has been described with respect to specific embodiments, many modifications, variations, alterations, substitutions, and equivalents will be apparent to those skilled in the art. Accordingly, the invention is to be considered as limited only by the spirit and scope of the appended claims.

What is claimed is:

1. A method for real-time tracking of catheter guide wires in fluoroscopic images during Interventional Radiological procedures utilizing a fluoroscopic examination system including a fluoroscope, an image digitizer with storage capability, and a live image video monitor, said method comprising the steps of storing said fluoroscopic images to a stored image video monitor:

extracting pixels from a digitized fluoroscopic image corresponding to the path of a catheter within a patient undergoing an interventional radiologic procedure by a) creating a binary peak image of said path of the catheter and b) constructing said a two-dimensional model of said catheter path from said binary peak image for output to said live video image monitor; and superimposing on said live image video monitor a visual representation of said catheter path onto a live fluoroscopic output image emanating from said fluoroscope.

2. The method of claim 1 wherein said constructing step comprises the steps of:

a) thinning said binary peak image;

b) ordering said thinned binary peak image into pixel chains;

c) organizing said pixel chains into first and second trees of pixel chains, wherein the nodes of said trees represent pixel chains, and wherein said first and second trees represent a first and second direction relative to the longest of said pixel chains and said both trees represent paths of semi-connected pixel chains;

d) searching said trees for longest valid paths through the nodes of said trees;

e) selecting the path having a minimum curvature if no single valid path is longest;

f) repeating steps c-e, using the next longest of said pixel chains in step c);

g) selecting the longest of the valid paths found in step d); and h) representing the longest valid path as a set of line segments.

3. An apparatus for real-time tracking of catheter guide wires in fluoroscopic images during Interventional Radiological procedures utilizing a fluoroscopic examination system including a fluoroscope, an image digitizer with storage capability, and a live image video monitor, said apparatus comprising:

a stored image video monitor for storing and displaying selected fluoroscopic images;

means for extracting pixels from a digitized fluoroscopic image corresponding to the path of a catheter within a patient undergoing an interventional radiological procedure; and means for superimposing on said live image video monitor a visual representation of said catheter path onto a fluoroscopic output image emanating from said fluoroscope.

4. An apparatus for real-time tracking of catheter guide wires in fluoroscopic images during Interventional Radiological procedures utilizing a fluoroscopic examination system including a fluoroscope, an image digitizer with storage capability, and a live image video monitor, said apparatus comprising means for storing said fluoroscopic images to a stored image video monitor;

means for extracting pixels from a digitized fluoroscopic image corresponding to the path of a catheter within a patient undergoing an interventional radiological procedure comprising a) means for creating a binary peak image of said path of said catheter and b) means for constructing a two-dimensional model of said catheter path from said binary peak image for output to said live video image monitor; and means for superimposing on said live image video monitor a visual representation of said catheter path onto a live fluoroscopic output image emanating from said fluoroscope.

5. The apparatus of claim 4 wherein said constructing means comprises:

a) means for thinning said binary peak image;
b) means for ordering said thinned binary peak image into pixel chains;
c) means for organizing said pixel chains into first and second trees of pixel chains, wherein said first and second tree represent a first and second direction relative to the longest of said pixel chains and said both trees represent paths of semi-connected pixel chains;
d) means for searching said trees for longest valid paths through the nodes of said trees;
e) means for selecting the path having a minimum curvature if no single valid path is longest;
f) means for repeating steps c-e using the next longest of said pixel chains in step c;
g) means for selecting the longest of the valid paths found in step d; and
h) means for representing said longest valid path as a set of line segments.

6. An apparatus for real-time tracking of catheter guide wires in fluoroscopic images during Interventional Radiological procedures utilizing a fluoroscopic examination system including a fluoroscope, an image digitizer with storage capability, and a live image video monitor, said apparatus comprising:
   a stored image video monitor for storing and displaying selected fluoroscopic images;
   a digital computer programmed to extract pixels from a digitized fluoroscopic image corresponding to the path of a catheter within a patient undergoing an interventional radiological procedure; and
   switching means for superimposing on said live image video monitor a visual representation of said catheter path onto a fluoroscopic output image emanating from said fluoroscope.

7. An apparatus for real-time tracking of catheter guide wires in fluoroscopic images during Interventional Radiological procedures utilizing a fluoroscopic examination system including a fluoroscope, an image digitizer with storage capability, a stored image video monitor and a live image video monitor, said apparatus comprising:
   a digital computer programmed to extract pixels from a digitized fluoroscopic image corresponding to the path of a catheter within a patient undergoing an interventional radiological procedure by
   a) creating a binary peak image of said path of said catheter and
   b) constructing a two-dimensional model of said catheter path from said binary peak image for output to said live video image monitor; and
   switching means for superimposing on said live image video monitor a visual representation of said catheter path onto a live fluoroscopic output image emanating from said fluoroscope.

8. The apparatus of claim 7 wherein said digital computer programmed to construct is programmed to:
   a) thin said binary peak image;
   b) order said thinned binary peak image into pixel chains;
   c) organized said pixel chains into first and second trees of pixel chains, wherein said first and second tree represent a first and second direction relative to the longest of said pixel chains and said both trees represent paths of semi-connected pixel chains;
   d) search said trees for longest valid paths through the nodes of said trees;
   e) select the path having a minimum curvature if no single valid path is longest;
   f) repeat steps c-e using the next longest of said pixel chains in step c;
   g) select the longest of the valid paths found in step d; and
   h) represent said longest valid path as a set of line segments.

* * * * *